US011662335B2

(12) United States Patent
MacNeill

(10) Patent No.: US 11,662,335 B2
(45) Date of Patent: May 30, 2023

(54) ION-PAIRING FREE LC-MS BIOANALYSIS OF OLIGONUCLEOTIDES

(71) Applicant: Laboratory Corporation of America Holdings, Burlington, NC (US)

(72) Inventor: Robert MacNeill, Monroe Township, NJ (US)

(73) Assignee: Laboratory Corporation of America Holdings, Burlington, NC (US)

( * ) Notice: Subject to any disclaimer, the term of this patent is extended or adjusted under 35 U.S.C. 154(b) by 80 days.

(21) Appl. No.: 16/900,165

(22) Filed: Jun. 12, 2020

(65) Prior Publication Data
US 2020/0393423 A1 Dec. 17, 2020

Related U.S. Application Data

(60) Provisional application No. 62/861,572, filed on Jun. 14, 2019.

(51) Int. Cl.
*G01N 30/02* (2006.01)
*C12N 15/10* (2006.01)
*G01N 1/40* (2006.01)

(52) U.S. Cl.
CPC ......... *G01N 30/02* (2013.01); *C12N 15/1017* (2013.01); *G01N 1/405* (2013.01); *G01N 2030/027* (2013.01); *G01N 2560/00* (2013.01)

(58) Field of Classification Search
CPC ........ G01N 30/02; G01N 1/405; G01N 27/62; G01N 2030/027; G01N 2560/00; G01N 30/72; G01N 30/88; G01N 2030/8827; C12N 15/1017
See application file for complete search history.

(56) References Cited

U.S. PATENT DOCUMENTS

| 7,341,840 | B2* | 3/2008 | Serhan | G01N 33/505 |
| | | | | 435/7.2 |
| 7,935,921 | B2* | 5/2011 | Grant | G01N 33/78 |
| | | | | 250/288 |
| 8,039,794 | B2* | 10/2011 | Haddon | B01D 59/44 |
| | | | | 435/193 |
| 2011/0240842 | A1* | 10/2011 | Grant | G01N 33/743 |
| | | | | 250/288 |

(Continued)

FOREIGN PATENT DOCUMENTS

| WO | 2008/057083 | 5/2008 |
| WO | 2009/032293 | 3/2009 |

OTHER PUBLICATIONS

"67th ASMS Conference on Mass Spectrometry and Allied Topic", Journal of the American Society for Mass Spectrometry, 30(1):180-216 (2019).

(Continued)

*Primary Examiner* — David A Vanore
(74) *Attorney, Agent, or Firm* — Kilpatrick Townsend & Stockton LLP

(57) ABSTRACT

Methods of LC-MS analysis of oligonucleotides free of ion-pairing reagents are disclosed herein. Historically, ion-pairing reagents have been used for acceptable extraction and chromatography prior to mass spectral analysis. The disclosure herein presents methods free of ion-pairing reagents at each stage, from extraction through the LC-MS endpoint. Also disclosed herein are systems for performing these methods.

4 Claims, 6 Drawing Sheets

RM1

VA1

(56) References Cited

U.S. PATENT DOCUMENTS

| | | | | |
|---|---|---|---|---|
| 2012/0261568 A1* | 10/2012 | Coon | ............ | G16B 40/10 |
| | | | | 250/288 |
| 2014/0038203 A1* | 2/2014 | Arthur | ............ | G01N 33/6893 |
| | | | | 435/7.1 |
| 2014/0096596 A1* | 4/2014 | Brousmiche | ............ | B01J 20/264 |
| | | | | 73/61.52 |
| 2014/0162248 A1* | 6/2014 | Cohen | ............ | B01D 15/08 |
| | | | | 536/23.1 |

OTHER PUBLICATIONS

Buszewski, B. and Noga, S., "Hydrophilic Interaction Liquid Chromatography (HILIC)—A Powerful Separation Technique", Anal, and Bioanal. Chem. 402(1):231-247 (2012).

Easter, R. et al., "Separation and Identification of Oligonucleotides by Hydrophilic Interaction Liquid Chromatography (HILIC)—Inductively Coupled Plasma Mass Spectrometry (ICPMS)", Analyst, 135(10):2560-2565 (2010).

Lobue, P. et al., "Oligonucleotide Analysis by Hydrophilic Interaction Liquid Chromatography-Mass Spectrometry in the Absence of Ion-Pair Reagents", J. Chromatogr. A, 1595:39-48 (2019).

PCT/US2020/037473, International Search Report and Written Opinion, dated Sep. 4, 2020, 13 pages.

CA 3,142,017, Office Action, dated Sep. 20, 2022, 3 pages.

PCT/US2020/037473, International Preliminary Report on Patentability, dated Dec. 23, 2021, 9 pages.

\* cited by examiner

ION-PAIRING FREE LC-MS BIOANALYSIS OF OLIGONUCLEOTIDES

RELATED APPLICATIONS

The present application claims priority to U.S. Provisional Patent Application No. 62/861,572, filed Jun. 14, 2019.

BACKGROUND

Historically, the bioanalysis of therapeutic oligonucleotides by liquid chromatography interfaced with mass spectrometry has been strongly associated with the use of ion-pairing reagents. These have been traditionally present not only in the LC-MS analytical endpoint, but in the preceding sample preparation as well, and ion-pairing has been operational at some point in all reported oligonucleotide LC-MS methods. Ion-pairing comes with associated phenomena like signal suppression and poor signal stability leading to poor reproducibility, reduced column lifetimes and increased instrumental down-time to remove ion-pairing residue.

A need exists for a quantitative LC-MS method for oligonucleotide analysis with a procedure liberated from ion-pairing at all stages.

SUMMARY

Disclosed herein are embodiments of a method of LC-MS analysis of oligonucleotides under ion-pairing free conditions.

In some embodiments, the method comprises providing a sample believed to contain at least one component of interest; conducting an extraction of the at least one component of interest under ion-pairing-free conditions, wherein the extraction is a solid phase extraction, and wherein the at least one component of interest is an oligonucleotide; separating the components via liquid chromatography under ion-pairing free conditions; and analyzing the components via mass spectral analysis under ion-pairing free conditions.

Also disclosed is are embodiments of a system for LC-MS analysis of oligonucleotides under ion-pairing free conditions.

DETAILED DESCRIPTION OF THE INVENTION

Figure 1:
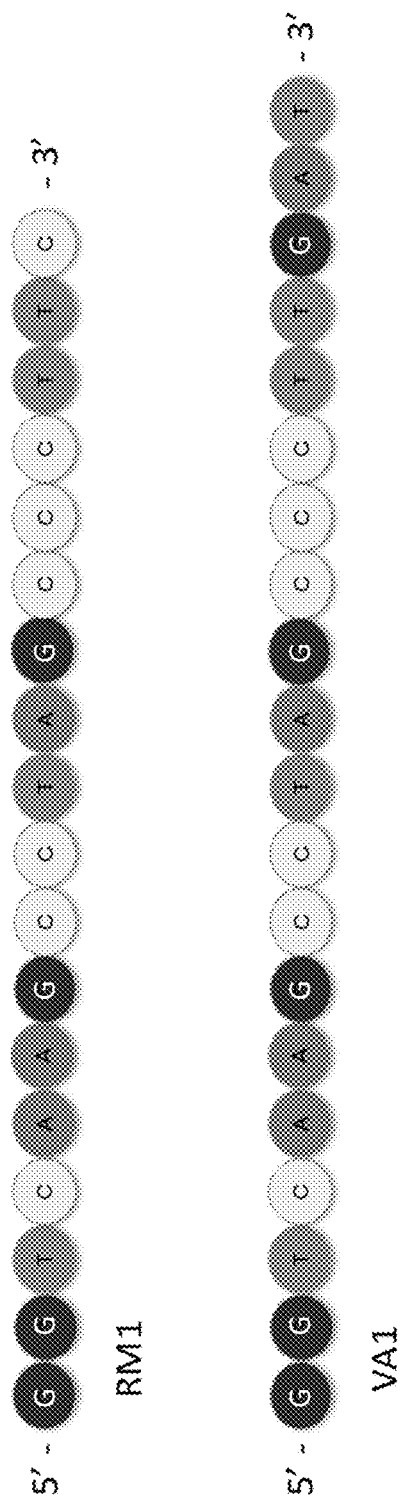
FIG. 1 depicts the sequences of oligonucleotide RM1 and an internal standard VA1.

The following description recites various aspects and embodiments of the present methods and systems. No particular embodiment is intended to define the scope of the methods and systems. Rather, the embodiments merely provide non-limiting examples of various methods and systems that are at least included within the scope of the methods and systems. The description is to be read from the perspective of one of ordinary skill in the art; therefore, information well known to the skilled artisan is not necessarily included.

Definitions

The present disclosure now will be described more fully hereinafter. The disclosure may be embodied in many different forms and should not be construed as limited to the aspects set forth herein; rather, these aspects are provided so that this disclosure will satisfy applicable legal requirements. Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

When introducing elements of the present disclosure or the embodiment(s) thereof, the articles "a", "an", "the" and "said" are intended to mean that there are one or more of the elements. The terms "comprising", "including" and "having" are intended to be inclusive and mean that there may be additional elements other than the listed elements. It is understood that aspects and embodiments of the disclosure described herein include "consisting" and/or "consisting essentially of" aspects and embodiments.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Embodiments of the present invention may be used to analyze a sample or biological sample. The sample may be in liquid, solid, and/or semi-solid form. The biological sample may include tissue, blood, biofluids, biosolids and the like as well as combinations thereof. Thus, the term "biological sample" includes, by way of example and without limitation, whole blood, plasma or serum, urine, cerebral spinal fluid (CSF), lymph samples, saliva, sputum, stool samples, lavages, semen, tissues, and/or body fluids and chemical constituents thereof in raw form and/or in preparations.

As used herein, the term "component of interest" or "biomarker of interest" is any marker that may provide biological information about the physiological state of an organism. In certain embodiments, the presence or absence of the biomarker may be informative. In other embodiments, the level of the biomarker may be informative. In an embodiment, the component of interest may comprise a peptide, a hormone, a nucleic acid, a lipid, or a protein. Or, other components of interest may be measured.

As used herein, the terms "subject" and "individual" may be used interchangeably. A subject may comprise an animal. Thus, in some embodiments, the sample is obtained from a mammalian animal, including, but not limited to a dog, a cat, a horse, a rat, a monkey, and the like. In some embodiments, the sample is obtained from a human subject. In some embodiments, the subject is a patient, that is, a living person presenting themselves in a clinical setting for diagnosis, prognosis, or treatment of a disease or condition.

As used herein, the terms "purify" or "separate" or derivations thereof do not necessarily refer to the removal of all materials other than the analyte(s) of interest from a sample matrix. Instead, in some embodiments, the terms "purify" or "separate" refer to a procedure that enriches the amount of one or more analytes of interest relative to one or more other components present in the sample matrix. In some embodiments, a "purification" or "separation" procedure can be used to remove one or more components of a sample that could interfere with the detection of the biomarker of interest, for example, one or more components that could interfere with detection of an analyte by mass spectrometry.

As used herein, "chromatography" refers to a process in which a chemical mixture carried by a liquid or gas is separated into components as a result of differential distribution of the chemical entities as they flow around or over a stationary liquid or solid phase.

As used herein, "liquid chromatography" (LC) means a process of selective retardation of one or more components of a fluid solution as the fluid percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and hydrophilic-interaction liquid chromatography (HILIC). HILIC is a potent chromatographic mode involving the combination of electrostatic interactions and partitioning between a water-enriched layer adsorbed to a polar stationary phase and a high-acetonitrile mobile phase, and where retention generally increases with analyte polarity.

As used herein, the term "analytical column" refers to a chromatography column having sufficient chromatographic plates to effect a separation of the components of a test sample matrix. Preferably, the components eluted from the analytical column are separated in such a way to allow the presence or amount of an analyte(s) of interest to be determined. In some embodiments, the analytical column comprises particles having an average diameter of about 5 μm. In some embodiments, the analytical column is a functionalized silica or polymer-silica hybrid, or a polymeric particle or monolithic silica stationary phase, such as a phenyl-hexyl functionalized analytical column.

As used herein, "ion-pairing reagents" are chemical additives salts that will bind electrostatically to solutes or analytes being chromatographed or subjected to other analytical processes according to the nominal chemistry of the ion-pair complex, thus allowing the manifestation of certain chromatographic modes. Examples of ion-pairing reagents include alkylsulfonates and alkylammonium salts.

Analytical columns can be distinguished from "extraction columns," which typically are used to separate or extract retained materials from non-retained materials to obtained a "purified" sample for further purification or analysis.

As used herein, "oligonucleotide therapeutics" may be short-chain DNA or RNA oligomers designed to interfere with the expression of disease-related protein. The sequences of the oligomers may be approximately 15 to 50 nucleotide units.

Method

Disclosed herein are embodiments of a method of LC-MS analysis of oligonucleotides under ion-pairing free conditions. In some embodiments, the method comprises providing a sample believed to contain at least one component of interest; conducting an extraction of the at least one component of interest under ion-pairing-free conditions, wherein the extraction is a solid phase extraction, and wherein the at least one component of interest is an oligonucleotide; separating the components via liquid chromatography under ion-pairing free conditions; and analyzing the components via mass spectral analysis under ion-pairing free conditions.

In some embodiments, the sample is a biological sample. In some embodiments, the biological sample is plasma.

In some embodiments, the oligonucleotide is a therapeutic oligonucleotide.

System

Also described are systems for performing the method disclosed herein. In some embodiments, the system comprises non ion-pairing reagents, a solid-phase extraction system, a liquid chromatography system, and a mass spectrometry detection system.

Various embodiments of the disclosure have been described herein. It should be recognized that these embodiments are merely illustrative of the present disclosure. Variations of those preferred embodiments may become apparent to those of ordinary skill in the art upon reading the foregoing description. It is expected that skilled artisans can employ such variations as appropriate, and the disclosure is intended to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated or otherwise clearly contradicted by context.

EXAMPLES

Example 1—Ion-Pairing Free Quantitative LC-SRM Method for a 5,436 Da 18-Mer Oligonucleotide in Human Plasma Chemicals & Materials The reference materials for the analyte, RM1, and the analogue internal standard, VA1, were obtained from Integrated DNA Technologies (Skokie, Ill., USA). The sequences of oligonucleotide RM1 and an internal standard VA1 are depicted in FIG. 1. Acetonitrile, concentrated phosphoric acid (85%), concentrated ammonium hydroxide (25%), concentrated formic acid and ammonium formate were all obtained from Sigma Aldrich and were LC-MS grade with the exception of phosphoric acid which was ACS grade. Water was purified in-house with a Thermo Scientific Barnstead Nanopure purification system by reverse-osmosis filtration and subsequent de-ionization to a resistivity of 18.2 MΩ cm. Control human plasma with $K_2$EDTA anticoagulant was obtained from BioIVT (Hicksville, N.Y., USA), including from six individual donors for the differential tests and selectivity, and from two hyperlipidemic individuals for the appropriate correlative testing.

Initial HILIC Feasibility Tests

To investigate the feasibility of HILIC without ion-pairing for oligonucleotides, initial work was done with a 200 nM dilution of Waters' MassPREP OST™ Standard oligonucleotide test mixture, containing a variety of thymidine (T-) sequences (15, 20, 25, 30 and 35-mer), and a scouting HILIC gradient. The diluent of the test mixture was 1:1 acetonitrile:0.02% ammonium hydroxide in 10 mM ammonium formate (aq). The gradient started without delay going linearly from 90% acetonitrile to 50% over 4.0 minutes. The analytical column was a Waters)(Bridge Amide, 3.5 µm 50×2.1 mm, temperature 30° C.; flow 0.6 mL/min, and the aqueous component of the mobile phase was 0.02% ammonium hydroxide in 10 mM ammonium formate (aq). The mass spectrometer was a Sciex 4000 in single ion monitoring (SIM) mode, monitoring a particularly intense cluster of ions at m/z 1510, m/z 1505, and m/z 1499, which correspond to the 30-mer with six charges, the 20-mer with four charges, and the triply charged 15-mer, respectively.

Figure 4:
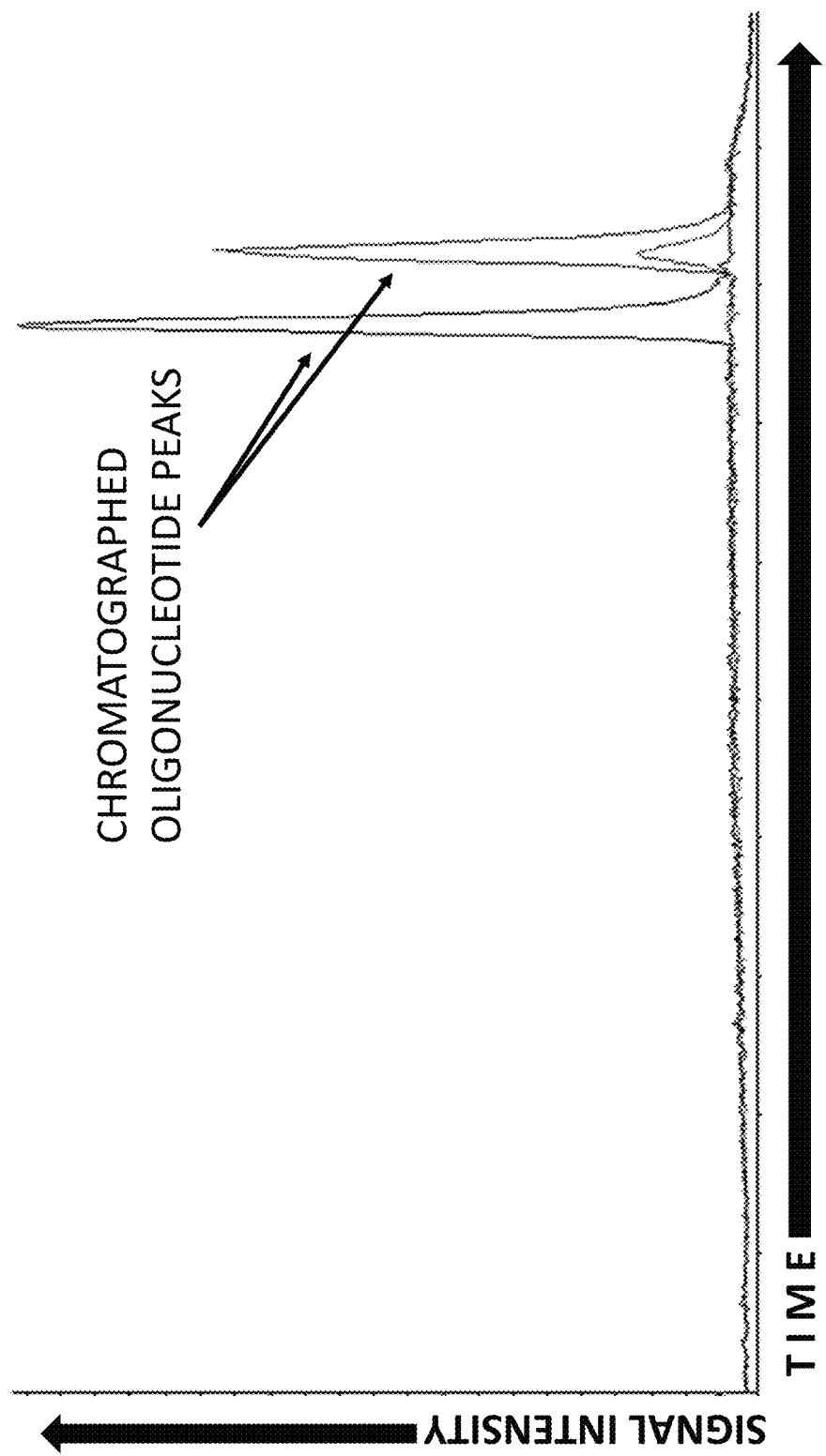
FIG. 4 is an hydrophilic interaction liquid chromatography (HILIC) chromatogram of a 200 nM dilution of Waters' MassPREP OST™ Standard oligonucleotide test mixture generated without ion-pairing at any step in accordance with an embodiment of the present disclosure.

The preliminary work using injections of the 200 nM dilution of Waters' MassPREP OST™ Standard oligonucleotide test mixture gave the chromatographic results evidence in FIG. 4. Three different thymine sequence components of the mixture could be easily traced in the SIM experiment used. The chromatography had clear integrity in terms of retention, peak symmetry, minimal band broadening, and response stability.

Figure 3:
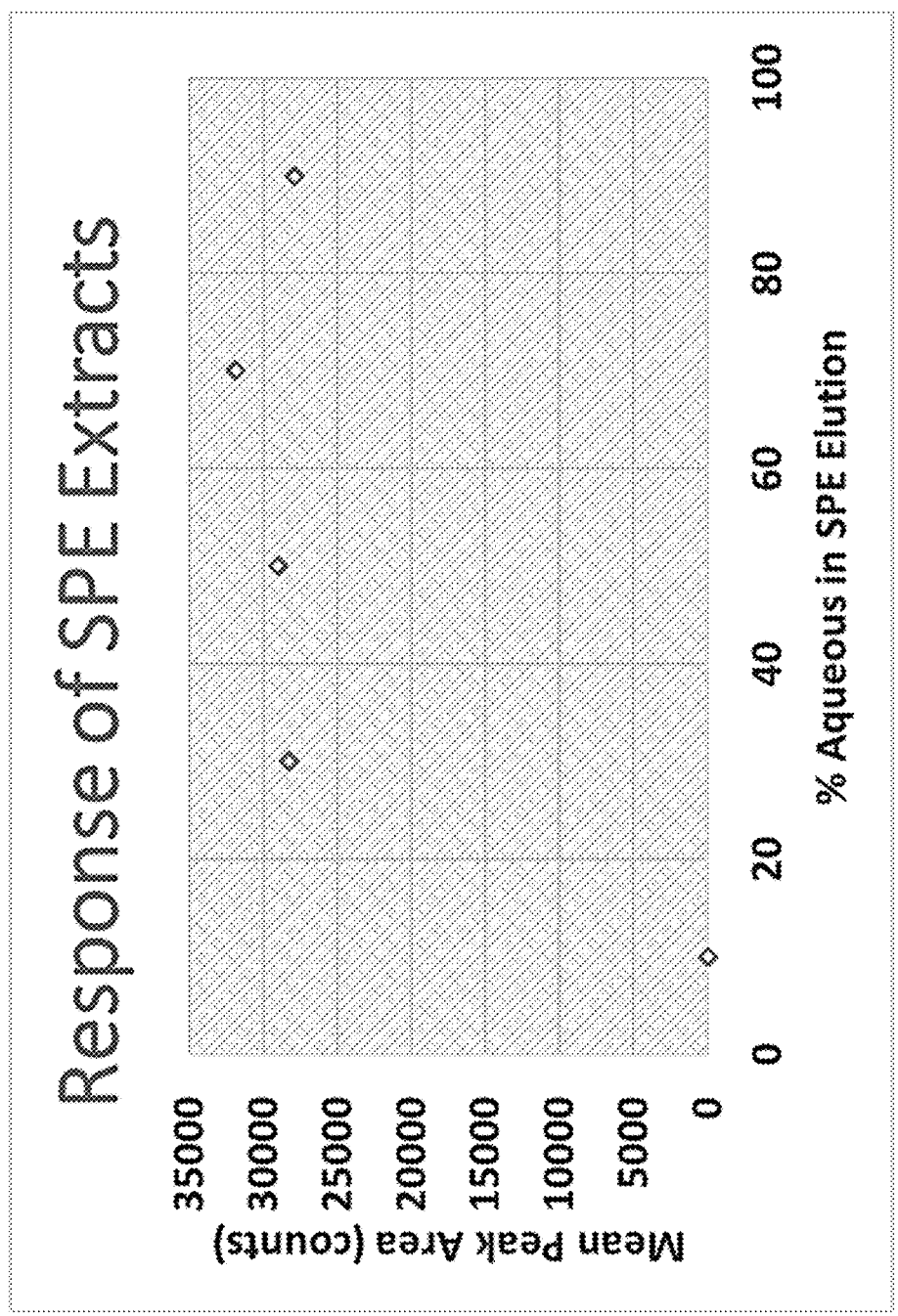
FIG. 3 shows the relative recovery of solid phase extraction (SPE) elution screens of different aqueous: organic compositions carried out in accordance with an embodiment of the present disclosure.

The wash and elution regime was optimized, progressing from high-aqueous acidic conditions to a highly basified elution after a mildly basic and high-organic second wash. The elution was in 70% aqueous as a result of screening of the elution conditions, which revealed zero recovery until a minimum of 30% aqueous level was reached, as is shown in FIG. 3.

Calibration Standards & Quality Control Samples

The RM1 primary solution and the internal standard VA1 primary solution were prepared at 200 µM and 100 µM, respectively, in 1:1 v:v water:acetonitrile. These primary solutions were prepared within the supplied vials containing 250 and 100 nanomoles of each compound, respectively, by reconstitution via the addition of the applicable 738 µL and 1000 µL of diluent followed by vortexing for 30 seconds. Calibration and QC sample spiking solutions, and the internal standard spiking solution, were prepared in 1:1 v:v water:acetonitrile, in polypropylene tubes. Plasma was prepared in analogous polypropylene tubes at concentrations of 10, 20, 50, 200, 500, 1000, 2500 and 5000 nM for calibrant samples and at 10, 20, 250 and 5000 nM for QC samples. Volumes of spiking solution were no more than 2% of the volume of plasma spiked. Blank hemolytic plasma was prepared for spiking by adding previously flash-frozen whole human blood to regular blank human plasma with $K_2$EDTA from the main stock, to a resultant hemolytic level of 2%.

Optimized Sample Preparation

The solid-phase extraction of RM1 and the analogue internal standard VA1 from human plasma was performed as follows. The SPE sorbent was Waters (Milford, Mass., USA) Oasis® WAX, 10 mg, a mixed-mode phase with cation exchange and reversed-phase moieties, in 96-well format. The 96-well 1 mL collection plates were regular inert polypropylene from Porvair (Wrexham, UK). Each step where liquid was applied was performed with the minimal aid of positive pressure to help percolation and passage of the liquid sample through the sorbent bed. The positive pressure manifold was from Agilent Technologies (Wilmington, Del., USA).

The analogue internal standard VA1, in 1:1 v:v acetonitrile:water at 2500 nM, was added in 20 µL aliquots to 100 µL plasma within 1.5 mL regular polypropylene tubes. This resulted in an internal standard concentration of 500 nM in matrix. Then, a two-second vortex of each tube took place. This was followed by the addition of 225 µL 4.5% $H_3PO_4$ (aq) to each sample and another vortex step.

Figure 2:
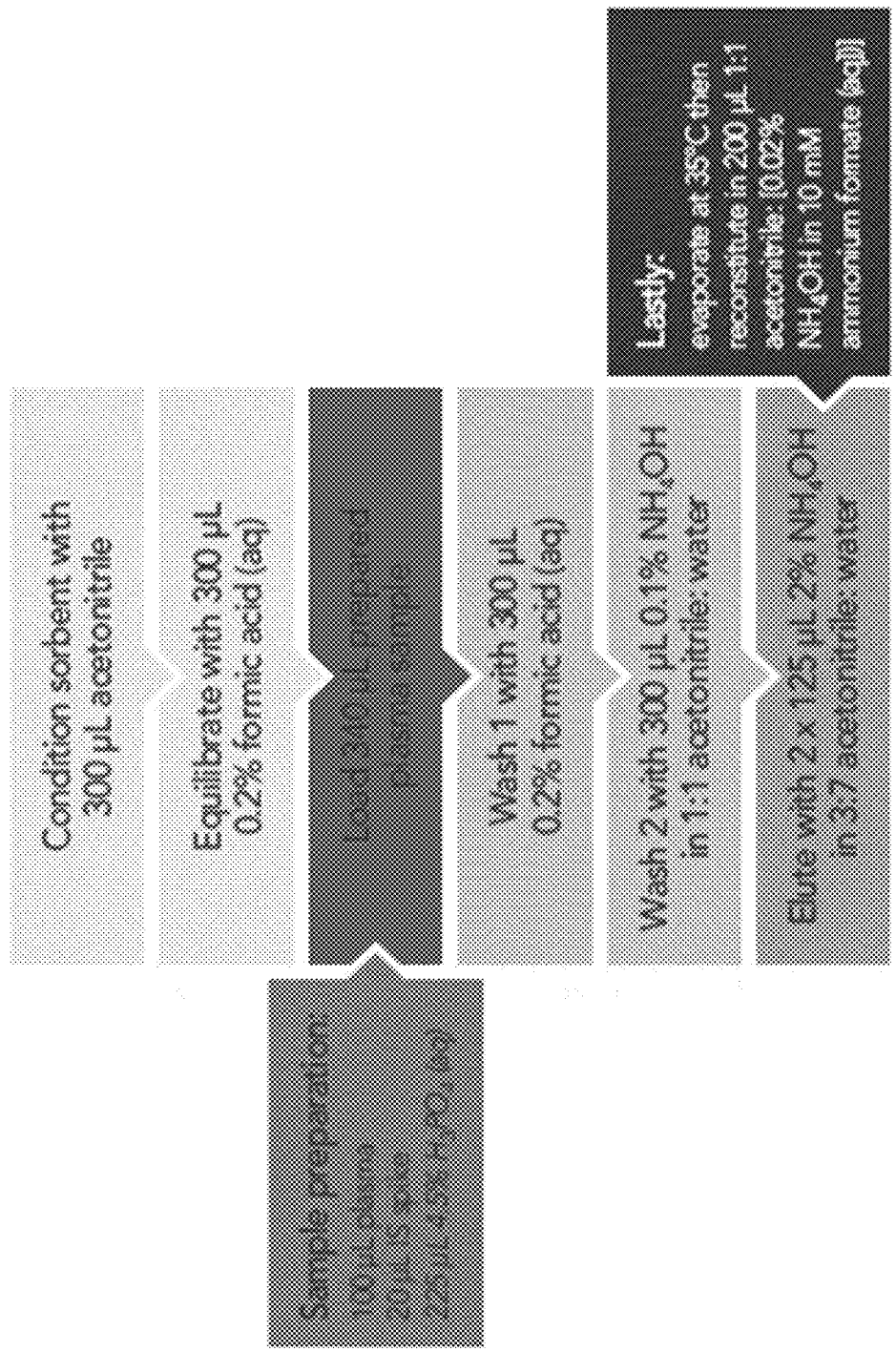
FIG. 2 depicts a sample preparation and extraction schematic in accordance with an embodiment of the present disclosure.

FIG. 2 depicts a sample preparation and extraction schematic in accordance with an embodiment of the present disclosure. The protocol begins with conditioning the sorbent with the application of 300 µL acetonitrile, and subsequent equilibration involved application of 300 µL 0.2% formic acid (aq). The prepared samples (340 µL) were loaded onto the equilibrated sorbent beds and this was followed by the application of a 300 µL wash with 0.2% formic acid (aq). The next wash was with 300 µL 0.1% ammonium hydroxide in [1:1 v:v acetonitrile:water]. Elution of the analyte and internal standard was effected by the application of 2×125 µL 2% ammonium hydroxide in [3:7 acetonitrile:water] into a 1 mL round-well regular polypropylene 96-well collection plate. Finally, the eluates were evaporated under oxygen-free nitrogen at 40° C. then reconstituted in 200 µL 1:1 acetonitrile:[0.02% ammonium hydroxide in 10 mM ammonium formate (aq)]. The block was then sealed, put on a plate shaker at 500 rpm for 20 minutes before being placed in the autosampler compartment at 10° C. awaiting injection. A wait period of 1 hour was undertaken prior to the onset of analysis to ensure temperature equilibration.

Optimized LC-SRM Analysis

The analytical column for RM1 quantification was a Waters (Milford, Mass., USA) Acquity UPLC BEH Amide with dimensions of 2.1×50 mm and 1.7 µm particle diameter. The LC-MS front end was a classic Waters Acquity UPLC system that included pump, degasser, autosampler, column heater and mobile phase pre-heater. The autosampler compartment was maintained at 10° C. Gradient elution was employed, with mobile phase components of 0.02% ammonium hydroxide in 10 mM ammonium formate (aq) and acetonitrile, delivered at 0.35 mL/min and with mobile and stationary phases both at 30° C. For each gradient cycle, initially the mobile phase composition began at 20% aqueous, and the mobile phase composition underwent a linear excursion over the next 3.5 minutes to 50% aqueous. This composition was held for 0.5 minutes then re-equilibration took place over the remaining 1.0 minutes of the 5-minute overall run time. The injection volume was 10.0 µL and partial loop with needle overfill (PLNO) mode was used, along with a strong wash composition of 0.02% ammonium hydroxide in 10 mM ammonium formate (aq) and a weak wash composition of 1:1 v:v acetonitrile:[0.02% ammonium hydroxide in 10 mM ammonium formate (aq)]. The triple quadrupole mass spectrometer was a Sciex (Concord, ON, Canada) API 6500+ with Turbo Ionspray source conditions and auxiliary gas heated to 550° C. On the IonDrive source, the probe positioning was 0 mm in the vertical and 7 mm in the horizontal. The instrument was operated in high mass mode. There was no split of the LC flow into the ion source.

In negative ion selected reaction monitoring (SRM) mode, the transitions used were summing 1358→914 and 1358→1059 for RM1, and summing 1522→634 and 1217→1074 for VA1, where all values denote m/z. All these peaks were selected on the basis of compelling intensity and verifiability. Both the analyte precursor ion at m/z 1358 and the internal standard precursor ion at m/z 1522 corresponded to the charge state of $[M-4H]^{4-}$, and the internal standard precursor ion at m/z 1217 corresponded to $[M-5H]^{5-}$. A comparison of the analytical conditions used in the initial qualitative HILIC tests and the RM1 fully quantitative methodology is summarized below in Table 1.

TABLE 2

Inter- and Intra-assay method performance

| Nominal concentration (nM) | 10 | 20 | 250 | 5000 |
|---|---|---|---|---|
| Intra-assay | | | | |
| Mean | 11.1 | 19.6 | 247 | 5510 |
| CV (%) | 5.16 | 2.75 | 4.79 | 4.14 |
| RE (%) | 10.7 | −2.08 | −1.07 | 10.1 |
| Inter-assay | | | | |
| Mean | 10.6 | 20.4 | 258 | 4990 |
| CV (%) | 9.50 | 5.73 | 5.64 | 9.66 |
| RE (%) | 6.21 | 1.89 | 3.00 | −0.211 |

Method performance: selectivity, differential matrix effect, matrix factor and recovery There was no significant manifestation of matrix effects, selectivity was also without issue, and recoveries at 50% were deemed acceptable.

The differential matrix effect samples altogether showed acceptable precision, demonstrating acceptability in terms of the nature and purpose of the test. Furthermore, the bias for each of the six was acceptable, an added indication of method ruggedness. The matrix factor results showed an overall value by ratio to be 1.05, and by peak areas alone as 0.92 for RM1 and 0.88 for VA1, all of which indicate a method effectively free of matrix-based signal alteration. These data are shown in Table 3.

TABLE 1

| LCMS Analytical Conditions | Initial Qualitative Test | RM1 Fully Quantitative Method |
|---|---|---|
| Front-end LC system | Waters Aquity UPLC ™ | Waters Acquity UPLC ™ |
| 96-well plate | 1 mL polypropylene round-well | 1 mL polypropylene round-well |
| A/S compartment temperature | 10° C. | 10° C. |
| Analytical column | Waters XBridge Amide 50 × 2.1 mm, 3.5 µm | Waters BHE Amide 50 × 2.1 mm, 1.7 µm |
| Flow rate | 0.6 mL/min | 0.35 mL/min |
| Mobile phase aqueous component | 0.02% NH$_4$OH in 10 mM ammonium formate | 0.02% NH$_4$OH in 10 mM ammonium formate |
| Mobile phase organic component | acetonitrile | acetonitrile |
| Column temperature | 30° C. | 30° C. |
| Gradient | 90% organic to 50% over 4.0 minutes, linearly no hold re-equilibration for 1.0 minutes | 80% organic to 50% over 3.5 minutes hold at 50% for 0.5 minutes re-equilibration for 1.0 minutes |
| Injection volume & mode | 10.0 µL partial loop with needle overfill | 10.0 µL partial loop with needle overfill |
| MS detector system | Sciex 6500 + triple quadrupole TurbolonSpray, negative ion mode SIM | Sciex 6500 + triple quadrupole TurbolonSpray, negative ion mode SRM |
| Monitoring (m/z) | 1510, 1505, 1499 | sum 1358 > 914 with 1358 > 1059 for RM1 sum 1522 > 634 with 1217 > 1074 for VA1 |

Method performance: inter-assay and intra-assay

Figure 5:
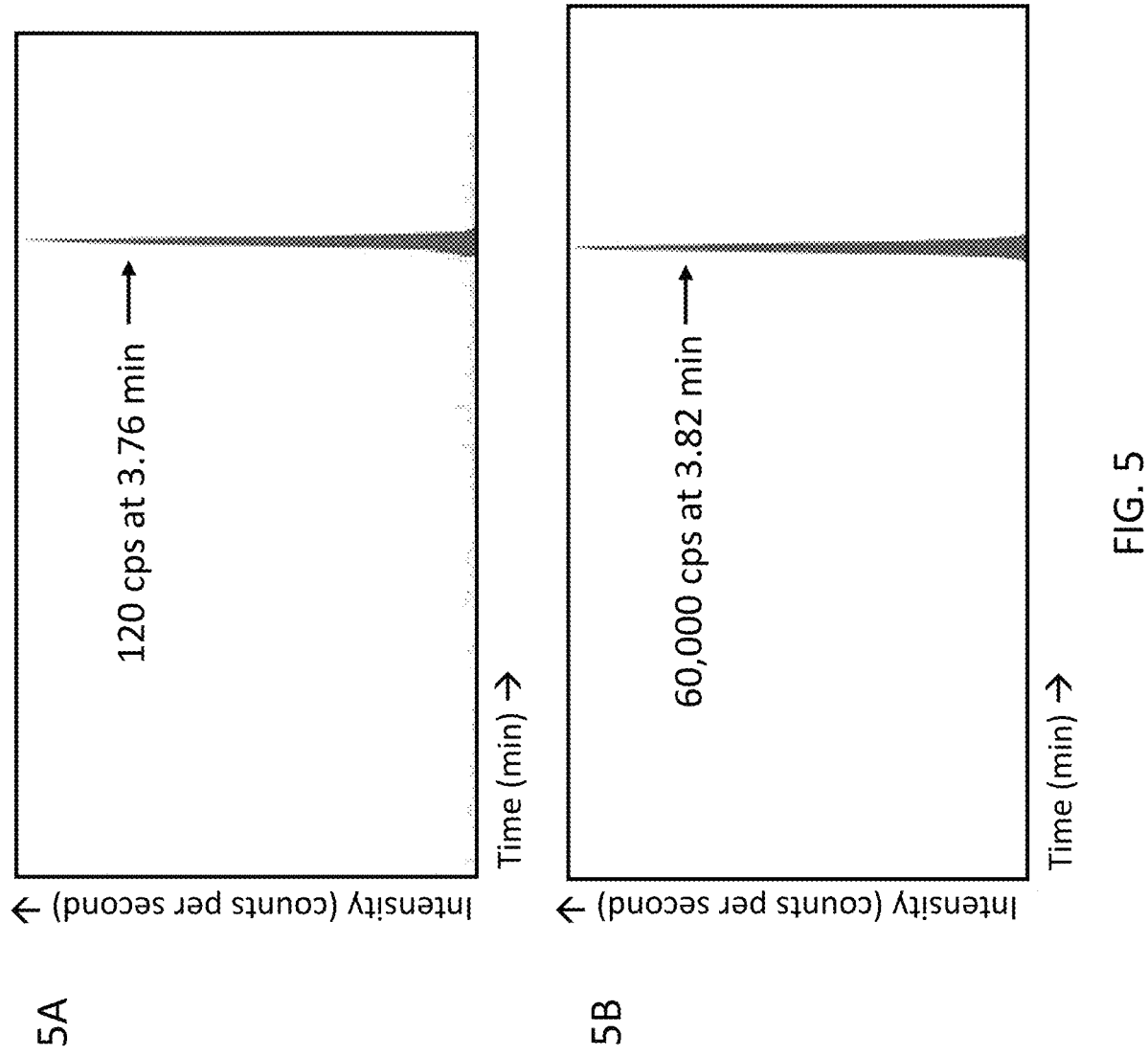
FIG. 5 shows representative chromatograms associated with the analyte RM1's lower limit of quantification (5A) and accompanying internal standard VA1 (5B) generated using an embodiment of the methods presented herein.
Figure 6:
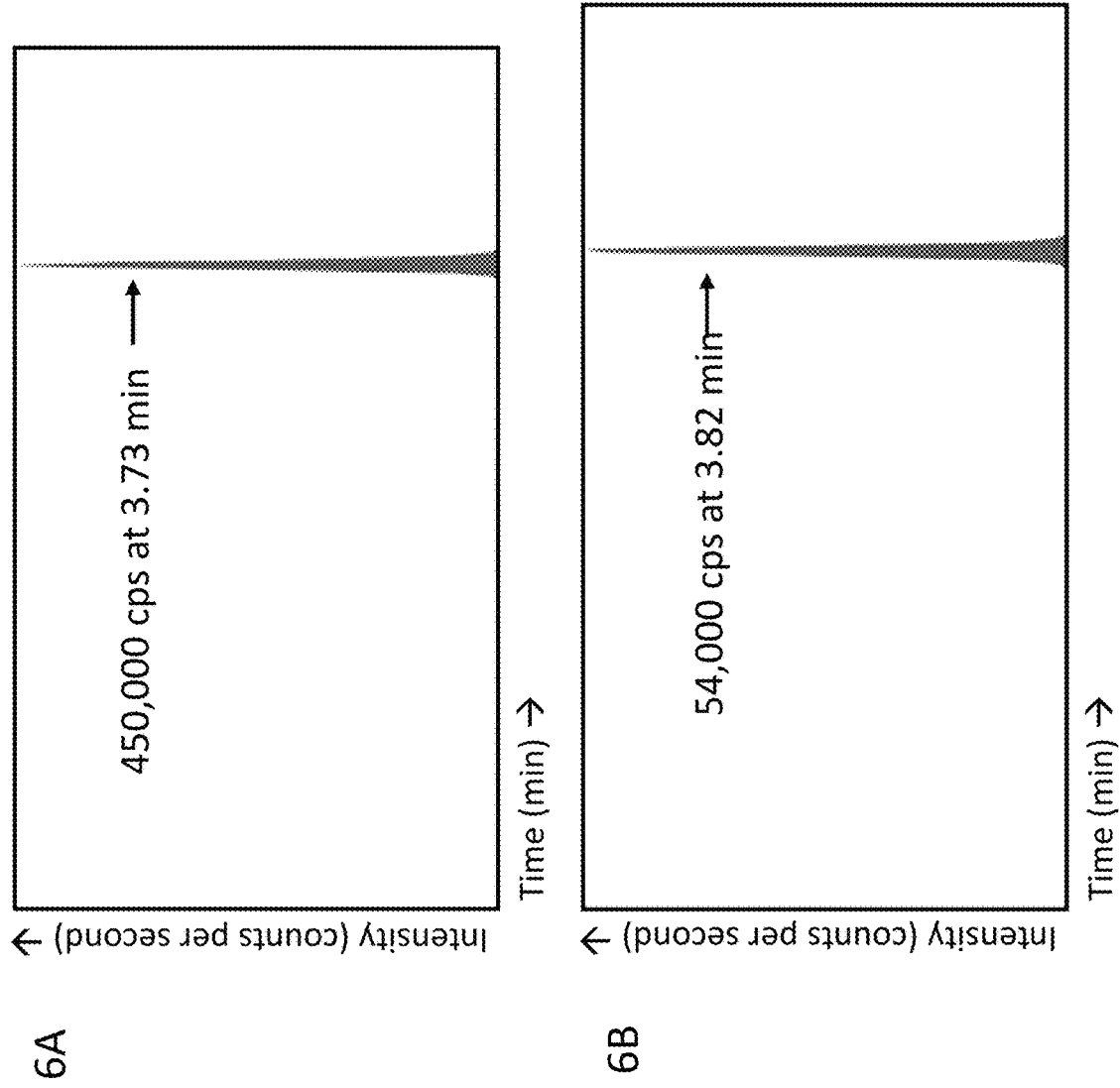
FIG. 6 shows representative chromatograms associated with RM1's upper limit of quantification (6A) and accompanying internal standard VA1 (6B) generated using an embodiment of the methods presented herein.

The methods described herein resulted in inter- and intra-assay accuracy and precision ranged from 97.9% to 111%, and 2.75% to 9.66%, respectively, over the calibration range of 10 nM to 5000 nM. This performance data is summarized below in Table 2. Chromatograms are shown in FIG. 5 and FIG. 6. FIG. 5 shows representative chromatograms associated with the analyte RM1's lower limit of quantification (5A) and accompanying internal standard VA1 (5B) generated using an embodiment of the methods presented herein. FIG. 6 shows representative chromatograms associated with RM1's upper limit of quantification (6A) and accompanying internal standard VA1 (6B) generated using an embodiment of the methods presented herein.

TABLE 3

Method Performance Metrics, nominal concentration 20 nM (LQC)

| | |
|---|---|
| Recover (%) - n = 6 | |
| Analyte | 50.4 |
| Internal standard | 46.1 |
| Differential matrix effect (CV) - n = 6 | |
| By ratio | 3.59 |
| Analyte: by area | 7.37 |
| IS: by area | 7.26 |
| Matrix factor - n = 6 | |
| By ratio | 1.05 |
| Analyte: by area | 0.921 |
| IS: by area | 0.881 |

TABLE 3-continued

| Method Performance Metrics, nominal concentration 20 nM (LQC) | |
| --- | --- |
| Hyperlipidemic effect - mean bias n = 2 | 17.8 |
| Hemolytic effect - mean bias n = 2 | 23.0 |

Example 2—Examples of Certain Embodiments

Listed hereafter are non-limiting examples of certain embodiments of the technology.

A1. A method comprising analyzing an oligonucleotide via LC-MS comprising:
 providing a sample believed to contain at least one component of interest;
 conducting an extraction of the at least one component of interest under ion-pairing-free conditions, wherein the extraction is a solid phase extraction, and wherein the at least one component of interest is an oligonucleotide;
 separating the components via liquid chromatography under ion-pairing free conditions; and
 analyzing the components via mass spectral analysis under ion-pairing free conditions.

A2. The method of embodiment A1, wherein the sample is a biological sample.

A3. The method of embodiment A2, wherein the biological sample is plasma.

A4. The method of embodiment A1, wherein the oligonucleotide is a therapeutic oligonucleotide.

B1. A system for performing the method of any of the preceding embodiments.

C1. A system for ion-pairing free analysis of oligonucleotides comprising
 non ion-pairing reagents;
 a solid-phase extraction system;
 a liquid chromatography system; and
 a mass spectrometry detection system.

That which is claimed is:

1. A method comprising analyzing an oligonucleotide via LC-MS comprising:
 providing a sample containing at least one oligonucleotide of interest;
 conducting an extraction of the at least one oligonucleotide of interest under ion-pairing-free conditions, wherein the extraction is a solid phase extraction;
 separating the at least one oligonucleotide of interest from other components of the sample via liquid chromatography under ion-pairing free conditions; and
 analyzing the at least one oligonucleotide of interest via mass spectral analysis under negative-ion mode and under ion-pairing free conditions.

2. The method of claim 1, wherein the sample is a biological sample.

3. The method of claim 2, wherein the biological sample is plasma.

4. The method of claim 1, wherein the oligonucleotide is a therapeutic nucleotide.

\* \* \* \* \*